(12) United States Patent
Piana et al.

(10) Patent No.: US 8,867,045 B2
(45) Date of Patent: Oct. 21, 2014

(54) TRIGGERING LIGHT GRID AND METHOD FOR DETERMINING THE POSITION OF CONTAINERS

(71) Applicant: Krones AG, Neutraubling (DE)

(72) Inventors: Stefan Piana, Köfering (DE); Thorsten Gut, Neutraubling (DE); Bernhard Dunzinger, Unterdegganbach (DE); Helmut Schäffer, Wenzenbach (DE)

(73) Assignee: Krones AG, Neutraubling (DE)

( * ) Notice: Subject to any disclaimer, the term of this patent is extended or adjusted under 35 U.S.C. 154(b) by 0 days.

(21) Appl. No.: 13/630,949

(22) Filed: Sep. 28, 2012

(65) Prior Publication Data

US 2013/0083330 A1    Apr. 4, 2013

(30) Foreign Application Priority Data

Sep. 29, 2011  (DE) .......................... 10 2011 083 757

(51) Int. Cl.
G01B 11/14 (2006.01)
G01V 8/20 (2006.01)
G01N 21/90 (2006.01)

(52) U.S. Cl.
CPC .............. *G01V 8/20* (2013.01); *G01N 21/9036* (2013.01); *G01B 11/14* (2013.01)
USPC ....................................................... 356/614

(58) Field of Classification Search
USPC ........... 356/615–622, 625, 635, 239.4, 239.5, 356/239.6, 240.1; 250/559.24, 559.29, 250/223 R, 223 B, 221
See application file for complete search history.

(56) References Cited

U.S. PATENT DOCUMENTS

| | | | | |
|---|---|---|---|---|
| 3,805,061 A | * | 4/1974 | De Missimy et al. | 250/208.3 |
| 4,107,523 A | * | 8/1978 | Corman | 250/223 B |
| 4,390,782 A | * | 6/1983 | Vornfett | 250/223 B |
| 5,015,840 A | * | 5/1991 | Blau | 250/221 |
| 5,204,911 A | * | 4/1993 | Schwartz et al. | 382/142 |

(Continued)

FOREIGN PATENT DOCUMENTS

| | | | |
|---|---|---|---|
| AT | 406577 B | 6/2000 | |
| DE | 4305559 A1 | 8/1994 | |
| DE | 4305559 A1 * | 8/1994 | G01V 9/04 |

(Continued)

OTHER PUBLICATIONS

Wynblatt "TOMTAC: Translating Object Motion to Actuator Control", May 2006.*
German Search Report for 102011083757.4, dated May 21, 2012.

*Primary Examiner* — Kara E Geisel
*Assistant Examiner* — Maurice Smith
(74) *Attorney, Agent, or Firm* — Marshall, Gerstein & Borun LLP (57) ABSTRACT

A triggering light grid and a method for registering the position of containers and/or for checking their alignment on a conveyance path. Due to the fact that a plurality of light barriers provided at different height levels with respect to the conveyance path and having light sources that can be activated separately of one another and a shared housing are provided, as is a triggering unit for the generation of control signals on the basis of output signals of the light barriers, different container types can be registered by reprogramming the triggering light grid without mechanical adjustment of the same.

20 Claims, 3 Drawing Sheets

(56) References Cited

U.S. PATENT DOCUMENTS

| | | | | |
|---|---|---|---|---|
| 5,266,810 A | * | 11/1993 | Murphy | 250/559.24 |
| 5,448,078 A | * | 9/1995 | Nakazawa | 250/559.24 |
| 5,923,428 A | * | 7/1999 | Woodworth | 356/623 |
| 6,046,834 A | * | 4/2000 | Asada et al. | 359/196.1 |
| 7,081,713 B2 | * | 7/2006 | Jurs et al. | 315/134 |

FOREIGN PATENT DOCUMENTS

| | | |
|---|---|---|
| DE | 10329881 A1 | 1/2005 |
| DE | 102005030829 B4 | 12/2009 |
| EP | 0801289 A2 | 10/1997 |
| EP | 1424296 B1 | 3/2006 |
| EP | 1873442 B2 | 12/2011 |

* cited by examiner

TRIGGERING LIGHT GRID AND METHOD FOR DETERMINING THE POSITION OF CONTAINERS

REFERENCE TO RELATED APPLICATIONS

The present application claims the benefit of priority of German Application No. 102011083757.4, filed Sep. 29, 2011. The entire text of the priority application is incorporated herein by reference in its entirety.

FIELD OF THE DISCLOSURE

The disclosure relates to a triggering light grid and to a method for determining the position of containers.

BACKGROUND DESCRIPTION OF THE RELATED ART

To manufacture containers and/or to fill products into containers, these containers are normally transported to the individual treatment stations in a continuous product flow on transporters, such as conveyor belts, for example. In order to ascertain the presence and/or the position of containers on transporters, triggering light barriers, for example, can be used. When an object passes through the light barrier, a trigger signal is then generated with which a subsequent treatment step and/or a purposeful forwarding of the detected container can be actuated. An inspection process can likewise be triggered or it can be ascertained whether or not a container is being transported in a proper, particularly upright, position.

For example, known from EP 08 01 289 A2 is a horizontal light curtain in which individual light barriers are arranged one behind the other in the conveying direction, so that a container passes through the individual light barriers one after the other. The light barriers are formed with the help of light guides, which are supplied from a common light source, and which are assigned receiver units. The light barriers detect at the height of the mouth area of the respective container type in order to make it possible to distinguish reliably between containers flowing in one behind the other. Detrimental in this arrangement, however, is that it is limited to a specific measurement height and consequently to a specific measuring task and specific container type.

Known from DE 43 05 559 A1 is a vertical light curtain in which a row-like arrangement of light transmitters is arranged on one side of a conveyor belt and a corresponding receiver row is arranged on the opposite side of the conveyor belt. Individual light barriers, arranged one behind the other in the conveying direction, are furthermore provided in order to determine the transport speed of the transport belt and the containers standing thereon. By means of repeated activation of the light transmitters, a container passing through the light curtain is scanned column by column, in order to create a contour grid of the container, with consideration given to the established conveying speed. This consequently involves a coarsely resolving imaging method, whereby each shaded light barrier segment generates the image points assigned to the container. By comparing these image points with "learned" comparison images, different container types can be distinguished from one another on the basis of their contours. Detrimental in this method, however, is that a comparatively large number of image points must be evaluated, so that the speed of the method is limited as a result. The containers must furthermore be a minimum distance apart from one another for the scanning, as a result of which the machine performance is additionally limited.

Vertical or slanted upright light grids are furthermore known from safety technology, for example from DE 103 29 881 A1 and DE 10 2005 030 829 B4, in order, for example, to detect or to distinguish between objects, such as auto bodies, and/or people on conveyor belts. For this purpose, light curtains are stretched transversely to the transport direction of a conveyor belt, whereby light sources are normally operated simultaneously one above another in a plurality of light barrier levels and a control signal is produced in the event of an inadmissible light attenuation level in one or more of the light barrier levels, for example, in order to switch off the production system for safety reasons. Due to the comparatively slow conveying speed in the case of such production processes and to the comparatively large dimensions of the objects or people to be monitored, a multitude of light barrier levels can easily be arranged one above another and evaluated together.

In filling systems, on the other hand, the position of containers with different shapes and sizes must be recognized reliably at comparatively high transport speeds in order for it to be possible to generate suitable control signals for subsequent production steps. For monitoring production sorted by type, height-adjustable light barriers, for example, are then provided that are to be adjusted to the respective container type. When there is a change in the product, adjustment mechanisms are consequently needed, as a result of which additional expenditure of labour results for the operation and servicing. Further disadvantages are the risk of operating mistakes, the only limited reproducibility due to mechanical hysteresis effects and mechanical wear of the adjustment mechanism.

In contrast, in the case of unsorted product processing, normally a plurality of triggering light barriers at different heights are combined together. Due to the comparatively large dimensions of the individual light barrier modules and the then necessary consolidation of individual controllers, there must be limitations when monitoring an unsorted production line in this way. For example, the light barrier modules cannot be arranged one above the other with the desired vertical resolution in a neck area of the containers that is especially important for detecting the position in order to make it possible to determine the position of different container types with sufficient reliability and flexibility.

There is therefore the need for a triggering light grid and a corresponding method for registering the position of containers with reliability and flexibility, with regard to different measuring tasks and container types, that are better than that of the state of the art.

The set task is solved with a triggering light grid according to the present disclosure, comprising a plurality of light barriers that are provided at different height levels with regard to the conveyance path and that have light sources that can be activated separately of one another and that are accommodated in a common housing. In this way, a compact light grid with an especially high vertical resolution level can be provided. Furthermore, the capability to activate the light sources separately allows the selection of different vertical light barrier areas, in order to solve specific measuring tasks. For example, the neck area of a container can be purposefully measured according to the shape and size of the incoming container type in order to ascertain a position of the container in the product flow. A side wall area of the container can likewise be purposefully measured in order to determine a maximum diameter of the container. Measurement signals from different height levels can likewise be registered simultaneously and compared to one another, in order, for example, to distinguish a proper upright position of the container from an improper reclining position.

A triggering unit for generating control signals on the basis of output signals of the light barriers is furthermore provided. It is consequently particularly possible to generate control signals assigned to individual containers. As a result, for example, a subsequent inspection can be adapted to the container type, the container can be purposefully forwarded and/or the container can be measured for a subsequent production step and its position in the product flow can be determined.

The light barriers comprise measurement beams that preferably are aligned parallel to one another. These preferably run transversely to the transport direction of the assigned conveyance means. On the basis of the capability for separated activation of the light sources, only those light sources have to be operated, and only those respective associated output signals of the respectively operated light barriers have to be evaluated, that are needed for a specific measuring task, for example, the determination of the position in the product flow. In this way, the measurement data processing can take place faster than in the case of a triggering light grid of the known construction, in which all light barrier levels are activated simultaneously and each of their output signals is evaluated. It is consequently possible to implement optimised combinations of individual light barriers with regard to a particular measuring task. For example, in one area of the light grid in which only a low vertical resolution level is needed, it would be possible to activate only every second or third light source.

The triggering unit is preferably formed for selective processing of individual output signals, particularly in order to process only output signals from those light barriers whose light sources have been activated. In this way, the processing time needed for the output of trigger signals can be adapted to the respective measuring task and, in particular, minimized. In particular, it is also possible for a plurality of measuring tasks to be solved simultaneously by means of activating light barriers in different height areas of the triggering light grid in groups and reading out and/or processing their output signals in groups. The number of light barriers needed for a measuring task and their resolution can hereby be adapted with the greatest possible flexibility without mechanical adjustment.

In an especially advantageous embodiment of the triggering unit according to the present disclosure, the output signals of selected light barriers can be evaluated together periodically within measurement cycles, each lasting a maximum of one millisecond, particularly in order to assign at least one individual control signal to each individual container. A control signal, for example, in the form of a suitable trigger edge, can consequently be output within one millisecond of the attenuation or interruption of the triggering light grid. This allows a sufficiently high response speed of the triggering light grid even at the transport speeds for containers customary in filling systems. To be understood as a control signal assigned to an individual container is a control signal that allows purposeful control of a subsequent production step or inspection step and/or purposeful forwarding or ejection of the container with regard to the product flow. The control signal can comprise characteristic information regarding the position and/or size of the container and or information regarding the proper or improper alignment of the container with respect to the product flow. The control signal is, in particular, a switch signal or trigger signal for a production unit or transport unit for the processing, inspection and/or filling of the containers. The control signal can be output both as a digital signal and via a bus with real-time capability, in which the control signal can be transmitted within a millisecond to the respective destination address for actuating an action.

Each of the output signals of the light barriers can be converted into logically usable measurement signals. A logically evaluable signal is understood, for example, as a status signal that, after comparison of the output signals with threshold values or the like, indicates whether or not an admissible light attenuation level in the area of a light barrier has been exceeded.

The triggering unit is preferably formed to evaluate and/or logically combine the output signals, in groups, of selected light barriers, or to generate at least two control signals assigned to a single container. In this way it is possible to combine different measurements within a single measurement cycle. For example, a first measurement can be made with a first light barrier group and simultaneously a second measurement can be made with a second measurement barrier group. The results of the light barrier groups can be evaluated independently of one another and/or compared to one another. This makes it possible, for example, to carry out a plausibility check or to attain additional information by combining measurement results. For example, by comparing the light attenuation level in an area of the container bottom and an area of the container neck, it can be ascertained whether or not a container is standing upright or is being transported in a reclining or slanted position. A position of the container, particularly with regard to a container main axis, can likewise be simultaneously determined and a characteristic container dimension, for example, a maximum diameter, can be determined simultaneously.

Individual measuring tasks can be combined in any way by forming groups of the activated light barriers. The resolution in individual light barrier groups can also be adapted purposefully depending on the measuring task that is to be solved. Furthermore, all light barriers of the triggering light grid can be used together, all light barrier levels of the triggering light grid can be distributed into groups or only selected light barriers of the triggering light grid can be grouped in a suitable manner for one or more measuring tasks. The number of light barriers needed for a specific measuring task, and consequently also the response time of the triggering light grid, can hereby be minimized.

In a particularly advantageous embodiment of the triggering light grid according to the present disclosure, the distance between neighbouring light sources amounts to a maximum of 10 mm, particularly a maximum of 5 mm. As a result, particularly critical container sections, such as neck areas of preserved food jars, for example, can also be measured with sufficient local resolution. This is particularly made possible by the combination of a plurality of light barriers in one shared housing. The shared housing allows an especially dense staggering of individual light barrier levels. The maximum distance is defined in each case between the optical centre axes of the light sources. Suitable light sources are LEDs, for example.

The triggering light grid preferably comprises at least one reflector in order to reverse measurement beams emitted by the light sources back towards the shared housing. In this way, active components, such as both the light sources and also assigned light receivers, can be accommodated compactly in a shared housing. This reduces the expenditure for the cabling and associated plug-in connections. Furthermore, because of the beam reversal, the measurement beams can be guided through the measurement field twice in the area of the conveying section. In this way, the measuring sensitivity and/or the actuation reliability of the triggering light grid can be improved when passing containers with low beam attenuation. Also within the scope of the present disclosure, however, is an arrangement in which the light sources are accommodated in a first shared housing and assigned light receivers are accommodated in a second shared housing. In this case, it is also possible to arrange the light sources and the light receivers on different sides of the conveyance path, so that the measurement beams pass through the measurement field in the area of the conveyance path only once.

The triggering unit is preferably formed to generate a control signal if at least one of the output signals corresponds to light attenuation of at least 5%, particularly of at least 25%, in the assigned light barrier. This allows the detection of transparent media. Because the measurement beams are normally attenuated by several percent with each interface transition of the measurement beams from air into the container wall and from the container wall into air, the measurement of transparent containers is possible with a high level of reliability, particularly when a plurality of light barrier levels are grouped together.

The light sources are preferably provided such that they are offset in the transport direction of the containers. For example, the measurement resolution can be increased in the vertical direction by having every second light source offset in the lateral direction. It is also conceivable hereby that the light sources are provided such that they are only offset with respect to one another in a height area provided particularly for this.

The object according to the present disclosure is furthermore solved with a method for registering the position of containers and/or for checking their alignment on a conveyance path in accordance with Claim 9. By means of the selective activation of individual light barriers and the evaluation of the associated output signals, different measuring tasks can be solved and/or specific measuring tasks can be adapted to different container types, by means of determining the light attenuation level in the stipulated height areas of the conveyance path. The comparison of the determined light attenuation level with at least one comparison value furthermore allows the generation of control signals in order to control purposefully individual containers on the basis of the comparison. This allows flexible product control in the case of both sorted and unsorted conveyance. In particular, there is no longer a need for a mechanical adjustment of different light barrier levels in order to generate trigger signals for changing measuring tasks and/or changing container types.

The height area is preferably given in dependence on a conveyed container type. For example, measurement ranges for determining the position of a container, for determining the diameter and/or for checking a correct conveyance orientation, particularly in the case of sorted conveyance, can be adapted to the respective container type and the time required for actuating a trigger signal can be minimized. However, a plurality of height areas can also be measured simultaneously, particularly in the case of unsorted conveyance, and an automatic detection function can be derived from the output signals of the respective height areas. For example, a container can be identified by a comparison of the output signals of a plurality of light barrier groups and simultaneously measured.

Values of the light attenuation levels in at least two height areas are preferably compared and/or logically processed together in order to determine a container type and/or to distinguish a correct conveyance orientation from an incorrect conveyance orientation. Plausibility checks can likewise be carried out by means of comparison of the output values of different height areas. A correct conveyance orientation is, for example, given in the case of a container that is standing upright. Incorrect conveyance orientations can be given, for example, by a reclining or a slanted upright container position.

Time points of the interruption and release of the light barriers are preferably measured in at least two height areas and calculated together, in order to determine the position of a reference point, a reference surface and/or the main axis of the containers. This allows a localization of axes of symmetry of the containers and the like, even in the case of a measurement on slanted upright container areas. For example, measurement results offset in time can be interpolated in order to improve the precision of a central triggering in the case of slanted upright container walls.

In an especially advantageous development of the method according to the present disclosure, the output signals are evaluated in groups assigned to height areas in order to determine at least two of the following parameters of the container by means of the light attenuation levels at different height areas: height; position in the product flow; characteristic contour; outer diameter; and upright/reclining conveyance position. A plurality of measuring tasks and/or complex measuring tasks can consequently be solved within a single measurement cycle. By means of purposeful activation of the light barriers of the respective height areas, the measurement signals can be optimized for the respective measuring tasks, the measurement signals can be evaluated in a particularly short time and the associated trigger signals can be actuated in a particularly short time.

The control signal is furthermore preferably generated on the basis of a measured displacement increment that is characteristic for the conveyance path, particularly for determining a container position and/or a container diameter. This allows an especially swift and flexible determination of container-typical parameters.

Advantageous embodiments of the present disclosure are depicted in the drawing.

DETAILED DESCRIPTION OF THE PREFERRED EMBODIMENTS

Figure 1:
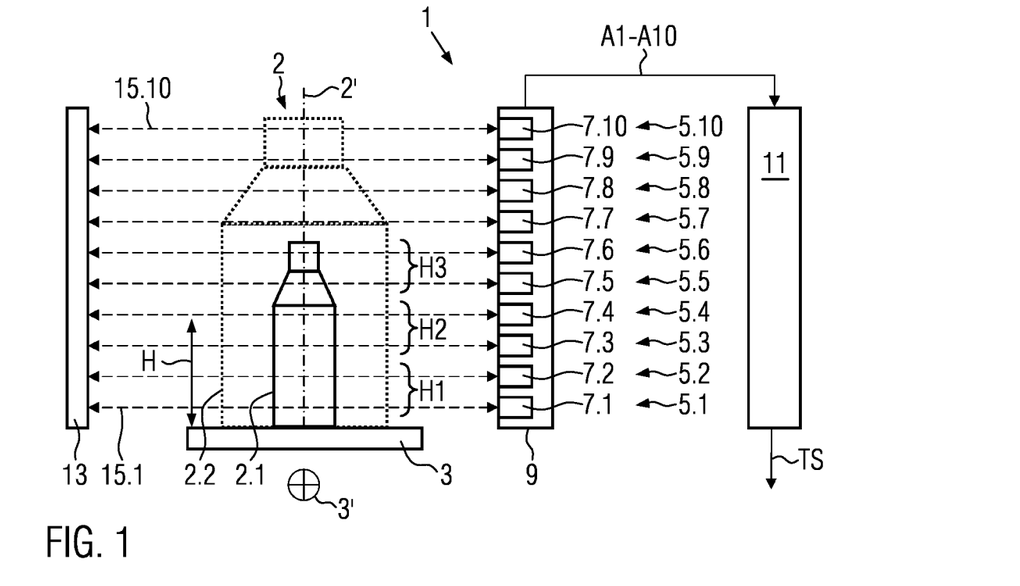
FIG. 1 is a cross-section through a first embodiment of the triggering light grid according to the present disclosure.

As can be seen in FIG. 1, the first embodiment 1 of the triggering light grid according to the present disclosure comprises, for acquiring the position P of containers 2 and/or for checking their alignment on a conveyance path 3, a plurality of light barriers 5.1 to 5.10 arranged at different height levels H with respect to the conveyance path 3, whereby each light barrier comprises light sources 7.1 to 7.10. These form the respective light transmitters of the light barriers 5.1 to 5.10 and are accommodated in a shared housing 9.

The light sources 7.1 to 7.10 can be activated individually and are connected to a triggering unit 11 for the generation of trigger signals TS, also called control signals in the following, on the basis of output signals A1 to A10 of the light barriers 5.1 to 5.10.

A continuous flow of containers 2 moves on the conveyance path 3, which is, for example, a conveyor belt or a rotation transporter, along the transport direction 3', in the example of FIG. 1, in the direction into the drawing plane. The light sources 7.1 to 7.10 are accordingly essentially aligned transversely and particularly orthogonally to the transport direction 3'. In the case of the first embodiment 1, the light barriers 5.1 to 5.10 work according to the reflection principle. A reflector 13 is accordingly provided across from the light sources 7.1 to 7.10, in order to reflect the measurement beams 15.1 to 15.10 emitted by the light sources 7.1 to 7.10 back in the direction of the housing 9, so that these beams pass through a measurement area above the conveyance path 3 twice. This is indicated in FIG. 2 schematically using the top-most measurement beam 15.10 of the associated light barrier 5.10.

Figure 2:
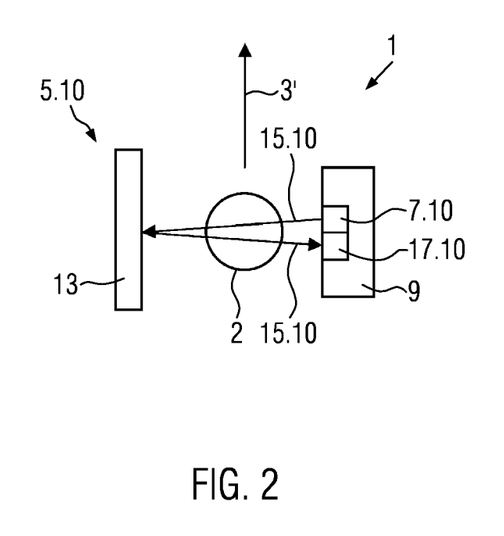
FIG. 2 is a top view on to a light barrier of the triggering light grid from FIG. 1.
Figure 3:
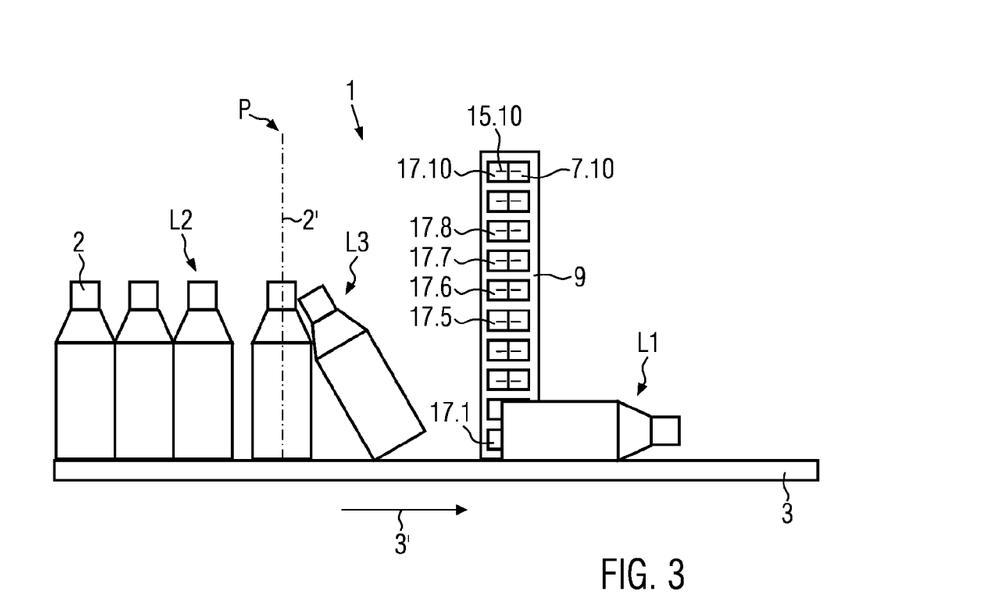
FIG. 3 is a longitudinal section through the triggering light grid from FIG. 1.

As can be seen in FIGS. 2 and 3, the light receivers 17.1 to 17.10 assigned to the light sources 7.1 to 7.10 are furthermore provided in the housing 9. These are likewise connected to the triggering unit 11, so that any selection of the output signals A1 to A10 can be transmitted to the triggering unit 11 within shared measurement cycles.

In the depicted example of FIG. 1, in the case of the sorted processing of a first container type 2.1, only the lower light sources 7.1 to 7.6 are activated and only the output signals of the light receivers 17.1 to 17.6 are read out and evaluated by the triggering unit 11. In contrast, the upper light sources 7.7 to 7.10 and the associated light receivers 17.7 to 17.10 lie in measurement areas above the containers 2 of the first container type 2.1 that is to be registered. Consequently no signal portion usable to register this container type 2.1 is to be expected from the upper light barriers 5.7 to 5.10. Only the lower light sources 7.1 to 7.6 are therefore preferably activated selectively. This does not, however, exclude an optional activation of further light sources.

In the case of sorted processing of a second container type 2.2, shown in dashes, for example, only the light sources 7.1, 7.5, 7.8 and 7.10 are activated and only the associated light receivers 17.1, 17.5, 17.8 and 17.10 are read out.

In the case of unsorted processing, all light barriers 5.1 to 5.10 could, for example, be operated. The advantage of the triggering light grid 1 according to the present disclosure lies, however, exactly in the fact that other combinations of activated and non-activated or read-out light barriers 5.1 to 5.10 are also possible as required without mechanical adjustment and with a comparatively high measurement resolution level.

A measurement cycle for reading out and evaluating all output signals A1 to A10 that are needed for the evaluation takes, for example, 0.2 to 2 ms. Particularly advantageous is a range of not more than 1 ms. Within this total cycle duration, on the one hand the positions P of individual containers 2 can also be determined with sufficient precision absolutely or with respect to the conveyance path 3 in the case of the transport speeds customary in filling systems. On the other hand, a sufficient number of output signals A1 to A10 of the light receivers 17.1 to 17.10 can also be read out and evaluated together within this cycle duration.

For example, within the preferred cycle duration, different measuring tasks can be carried out in parallel by activating selected light barriers 5.1 to 5.10. A specific measuring task can likewise be solved with the greatest possible precision, particularly with particularly good measurement resolution. Individual light barriers 5.1 to 5.10 can, for example, be read out one after the other, whereby within the total cycle duration of the triggering light grid 1 then, for example, up to 128 light barriers 5.1 to 5.10 could be read out and evaluated together.

Within the entire cycle duration of not more than 1 ms, preferably a suitable trigger signal TS can be output, for example, in the form of a suitable trigger edge. In this way, a subsequent production step, such as, for example, a forwarding, further processing or inspection of the respective container 2, can be individually controlled.

The output signals A1 to A10 of the individually activated light barriers 5.1 to 5.10 can be selected, calculated together and/or logically combined in any way. As a result, it is possible to derive purposefully a trigger function from particularly suitable height areas H1 to H3 of the triggering light grid 1. Conceivable, for example, is a so-called ordering of measurement signals, meaning that a trigger signal TS is generated as soon as there is an interruption in the measurement beam of a single light barrier that belongs to a group of light barriers formed for a specific measuring task, for example, the light barrier 5.1 or 5.2 for measuring a lower height area H1.

A further possible signal linking is so-called rounding, in which all measurement beams of a group of light barriers, for example, the light barriers 5.1 and 5.2 of the lowest height area H1, must be interrupted in order to actuate a trigger signal TS. In this way, the probability of erroneous triggering can be reduced. Such a rounding can likewise be used in order to reduce disturbances from objects that, for example, can stick out from the container 2. Then, for example, there would have to be an interruption in all measurement beams 15.1 to 15.4 of a group of light barriers 5.1 to 5.4 whose measurement area in the vertical direction is greater than the largest disturbance object, which, for example, could be a label that sticks out, to be expected. In this way, swing tops or straws can likewise be detected and/or excluded from the triggering. To avoid erroneous triggering, a specific minimum number of measurement beams 15.1 to 15.4 to be interrupted could also be stipulated within a stipulated group of light barriers 5.1 to 5.4, such as for example for the indicated height areas H1 and H2.

The processing of the output signals A1 to A10 of the light receivers 17.1 to 17.10 consequently preferably comprises a logical combination in order to reduce the risk of erroneous triggering and/or to solve specific measuring tasks. For example, this could also be the registering of a rotational position of containers with an asymmetrical cross-section. An example of this would be a one-sided handle opening (not shown) in the container, which in comparison to the container areas formed symmetrically in the cross-section, would cause characteristic light attenuation in certain light barrier levels.

The generation of at least two trigger signals from different height areas H1 to H3 of the triggering light grid 1 would also be an alternative or supplement to a logical combination of output signals A1 to A10 of individual light receivers 17.1 to 17.10. For example, this can then be advantageous if certain light barriers 5.1 to 5.10 of the triggering light grid 1 can be permanently assigned to a measuring task and/or parallel processing of a plurality of individual trigger signals TS is faster than the processing and/or combination of a plurality of necessary output signals A1 to A10 into a single trigger signal TS. In general, however, a selective use of individual light barriers 5.1 to 5.10, which means the selective activation of the associated light sources 7.1 to 7.10 and/or the selective read out of the output signals A1 to A10 supplied by the associated light receivers 17.1 to 17.10, allows an especially versatile registration of the position P, of the size and/or of the orientation of the containers 2. Likewise, different height areas H1 to H3 of the triggering light grid 1 can be used for different measuring tasks.

A further possibility for the logical combination of output signals A1 to A10 of individual light barriers 5.1 to 5.10 is indicated in FIG. 3. This shows a container 2 in a reclining, improper transport orientation L1. In this case, for example, with the help of a first group comprising the lower light barriers 5.1 and 5.2, a first shared evaluation result could be derived from the associated output signals A1 and A2, and, with the help of the light barriers 5.3 to 5.6 located above these, a second evaluation result, that can be calculated with or compared to the first evaluation result, can be derived from the associated output signals A3 to A6. For example, if a relevant light attenuation level is established in the first evaluation result but not in the second evaluation result, a reclining container 2 can be concluded. In contrast, in the case of a proper orientation L2 of a container 2 transported in an upright position, a relevant light attenuation level would have to be ascertained in both the first and the second evaluation result.

In the case of unsorted transport, which is indicated in FIG. 1 with the help of the two differently sized containers 2.1 and 2.2, for example, all light barriers 5.1 to 5.10 could be activated simultaneously and each could be evaluated separately. For example, the first container type 2.1 could be recognized by the fact that no relevant attenuation level is registered above the light barrier 5.6, but such an attenuation level is registered by the light barrier 5.6. A container position P with regard to the product flow could then, for example, be registered on the basis of the top-most light barrier 5.6 that is just barely still shaded.

To determine a container position P in the running product flow, it can furthermore be advantageous to compare at least one of the measured output signals A1 to A10 of the light receivers 17.1 to 17.10 to a displacement increment signal of the conveyance path 3, or to calculate said signal with said displacement increment signal. For example, a trigger signal TS could be provided after a delay in order to synchronize the trigger time point with the position of the container main axis 2'. For example, this would allow an ejection function to be set up then with respect to the container main axis 2'. This would be useful particularly in the case of unsorted transport.

The light barriers 5.1 to 5.10 are preferably aligned orthogonally to the transport direction 3' and to the main axis 2' of the containers 2 in the case of the proper container orientation L2. The triggering light grid 1 according to the present disclosure is, however, not restricted to such an orthogonal alignment. In the case of the reflection arrangement of the first embodiment, a slight tipping of the measurement beams 15.1 to 15.10 necessarily results from the side-by-side arrangement of the light sources 7.1 to 7.10 and the light receivers 17.1 to 17.10 before the reflection in comparison to the beam course after the reflection, as is indicated in FIG. 2. Uninterrupted measurement beams are therefore indicated in both FIGS. 3 and 4 by a horizontal connection line between the light source and the receiver.

The measurement area covered by the light barriers 5.1 to 5.10 preferably has a vertical extension of 100 mm to 500 mm. This allows most common container types to be registered. A measurement area from 200 mm to 400 mm high is particularly advantageous. The distances between neighbouring light barriers 5.1 to 5.10 preferably do not amount to more than 10 mm, particularly not more than 5 mm, in each case measured between the optical axes of the measurement beams 15.1 to 15.10.

The number of depicted light barriers 5.1 to 5.10 is only by way of example. In principle, any number of light barriers that can be activated selectively could be combined into a triggering light grid according to the present disclosure. Particularly practicable are, depending on the requirement, triggering light grids with at least 16 or at least 32 light sources that can be activated selectively. For improved flexibility with regard to different measurement areas and/or container types, row-like arrangements with at least 64, particularly at least 128 light sources or light barriers that can be activated selectively are especially suitable.

Figure 4:
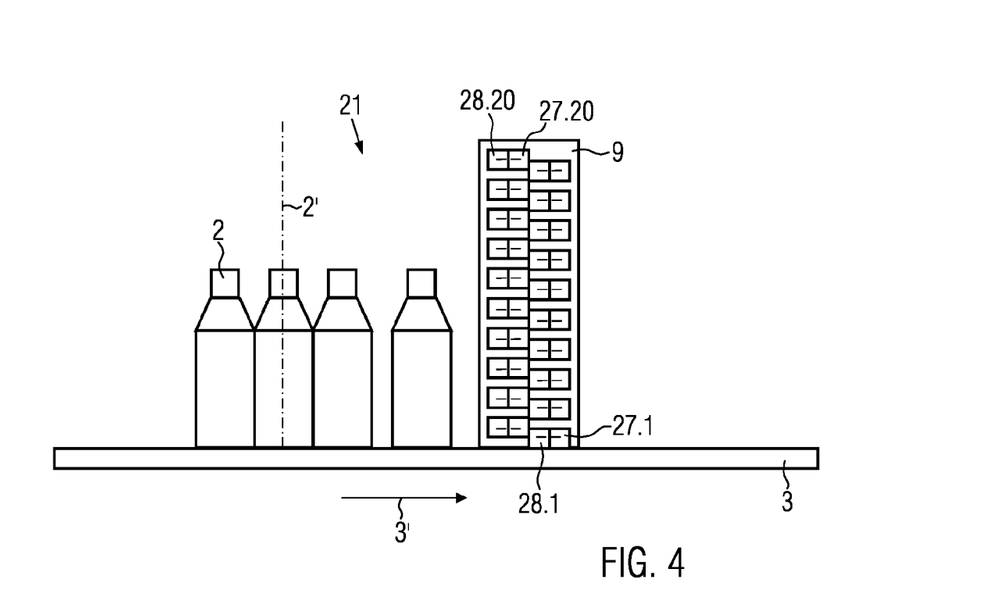
FIG. 4 is a longitudinal section through a second embodiment of the triggering light grid according to the present disclosure.

FIG. 4 shows a second embodiment 21 of the triggering light grid according to the present disclosure, in which the light sources 27.1 to 27.20 are arranged such that they are offset from one another when seen in the transport direction 3'. This can be advantageous, for example, when the vertical resolution of the associated light barriers should be less than the vertical dimensions of individual light sources 27.1 to 27.20. As in the first embodiment, light receivers 28.1 to 28.20 are assigned to the light sources, which act as transmitters.

Figure 5:
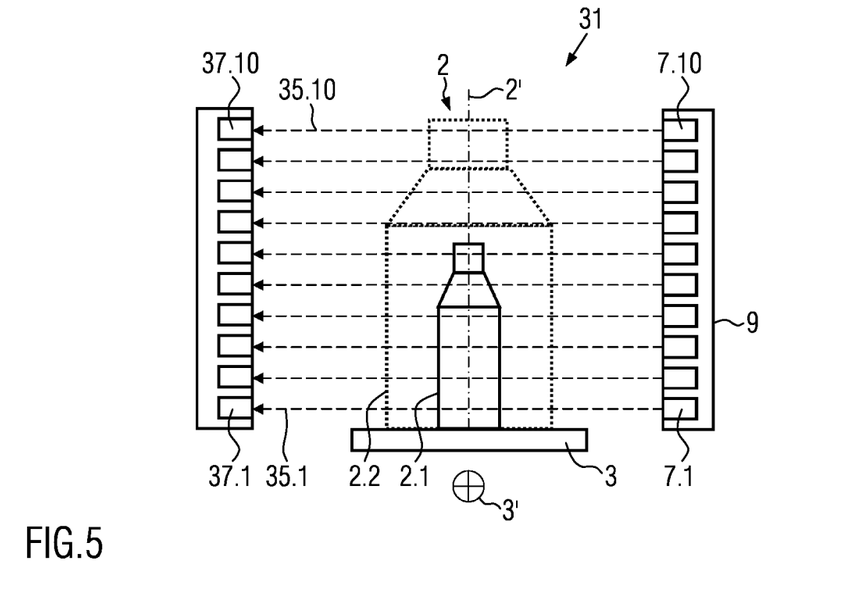
FIG. 5 is a cross-section through a third embodiment of the triggering light grid according to the present disclosure.

FIG. 5 shows a third embodiment 31 of the triggering light grid according to the present disclosure, in which the light sources 7.1 to 7.10 and the light receivers 37.1 to 37.10 are provided such that they lie opposite one another on different sides of the transport section 3. In principle, the same advantages can be achieved with this embodiment 31 as with the first embodiment 1 according to the reflection principle. However the associated measurement beams 35.1 to 35.10 in the third embodiment are less strongly attenuated by the containers 2 than, for example, in the first embodiment 1. The first embodiment 1 is accordingly better suited for transparent containers 2 with low levels of light attenuation. Furthermore, a particularly compact construction is made possible. The triggering unit 11 is not depicted in FIGS. 2 to 5 for the sake of clarity.

With the described embodiments 1, 21 and 31, which can also be combined in any technically expedient manner, the following improvements over the known state of the art can be achieved. A mechanical adjustment of individual light barriers depending on the respective container size that is to be registered is dispensable. Instead, a rigid attachment of the triggering light grid according to the present disclosure is possible. This improves the mechanical stability of the triggering light grid and improves the reproducibility of individual measurements. Production changes between different container types can be carried out faster and more flexibly. The reproducibility of the individual measurements is also given after repeated changeovers to changing container types. Mechanical wear due to changeovers to different container types can be avoided. The wiring effort can be minimized due to the integration of a plurality of light sources within a shared housing. The space requirement is considerably less than that with mechanical height adjustment. The cabling in an area above the transporter can likewise be minimized, as a result of which measures for protecting the cabling from glass breakage can be reduced or avoided. By using conventional field bus interfaces, such as, for example, CANopen, it is possible to implement diverse diagnostic functions and a software-controlled learning mode. A bus with real-time capability and a transmission time of not more than 1 ms is particularly suitable. Due to the varied possibilities of the logical combination of the output signals or measurement results of individual light barriers, the widest ranges of container characteristics, but also partial dirtying and the like, can be detected with increased reliability of the triggering and protection against erroneous triggering. The integration of light sources and light receivers in a shared housing simplifies the cleaning and compliance with hygiene requirements.

The working method of the triggering light grid according to the present disclosure is described by way of example using the first embodiment 1 for a sorted product flow:

Upright standing containers 2 of the container type 2.1 are continually passed through the triggering light grid 1 on the conveyance path 3. The light barriers 5.1 to 5.4 and 5.6 are activated selectively. The output signals of the associated light receivers 17.1 to 17.4 and 17.6 are read out selectively and combined into groups as follows for the evaluation in the triggering unit 11. A first group is formed from the lower light barriers 5.1 and 5.2. A second group is formed from the middle light barriers 5.3 and 5.4. The light barriers 5.7 to 5.10 lie in an area above the container 2 and are therefore not needed for the measurement of the containers 2. The light barrier 5.5 in the area of the container shoulder is likewise not needed in the example and is therefore not activated.

The lower light barriers 5.1 and 5.2 supply output signals A1 and A2 in order to register the presence of a container 2 on the conveyance path 3 regardless of its orientation on the conveyance path 3. In other words, the container 2 causes a relevant light attenuation level in the area of the lower light barriers 5.1 and 5.2, no matter whether it is in an upright standing position L2, in a slanted upright position L3 or in a reclining position L1. The presence of the container 2 on the conveyance path 3 can consequently be determined using at least one of the output signals A1 and A2 of the light barriers 5.1 and 5.2. These output signals A1 and A2 are, however, preferably evaluated together, for example, by having both light barriers 5.1 and 5.2 have to register a light attenuation level that lies above a stipulated threshold value.

The output signals A3 and A4 of the middle light barriers 5.3 and 5.4 can, for example, be used for a measurement of the container diameter. These output signals can furthermore be logically combined with the output signals A1 and A2 of the lower light barriers 5.1 and 5.2 in order to determine the orientation of the container 2 on the conveyance path 3. For example, by comparing and/or combining the output signals A1, A2 of the first light barrier group and the output signals A3, A4 of the second light barrier group, it is possible to distinguish whether or not the container 2 is being transported on the conveyance path 3 in a proper orientation L2. It is consequently possible to compare to one another, calculate together and/or logically combine in any way the output signals A1 to A4 of the individual light barrier groups, as well as to compare to one another, calculate together and/or logically combine in any way the already evaluated measurement results of the light barrier groups.

The top-most activated light barrier 5.6, which covers an upper height area H3, is particularly well-suited for determining the position P of the container 2 as an absolute value or with respect to the product flow, meaning the position of the container 2 in the transport direction 3'. For example, the time points of the light barrier interruption and the following release of the measurement beam 15.6 are measured. The output signal of the upper light barrier 5.6 can also be calculated with or compared to other output signals A1 to A4 and/or it can be logically combined with measurement results assigned to other light barrier groups.

The described group-by-group evaluation can preferably be adapted to changed production conditions by means of appropriate control commands at the software level, so that diverse possibilities for the use of any height areas H1 to H3 of the triggering light grid 1 exist without mechanical adjustment.

The triggering light grid 1 is operated continually during the passage of the container 2 through strung-together measurement cycles in each of which the light sources 7.1 to 7.10 are activated selectively and the associated output signals A1 to A10 are evaluated. Within each measurement cycle, a decision is made as to whether or not to output a trigger signal TS, which is assigned to the respective container 2.

A trigger signal TS is output, for example, if a threshold value of the light attenuation level is exceeded in at least one of the light barriers 5.1 to 5.10. Depending on the type of measuring task that forms the basis of the output of the trigger signal TS, for example, determining the position of the container 2 in the product flow or checking a proper orientation L2 of the container 2 on the conveyance path 3, trigger signals TS can be actuated for switching different production steps. The trigger signal TS can, for example, be a switch signal for ejecting the container 2 from the product flow, in the event that an improper orientation L1, L3 of the container 2 on the conveyance path 3 is ascertained. The trigger signal TS can likewise be a switch signal for actuating an inspection or a subsequent production step for which the position of the container 2 in the product flow must be known.

At least one of the output signals A1 to A10 of the light barriers 5.1 to 5.10 can likewise be combined with an output signal of a displacement increment encoder of the conveyance path 3. In this way, trigger signals TS can be actuated for actions that are delayed in time. In other words, it is possible not only to determine the current position of the container 2 but also a future position after passage through a defined section of the conveyance path 3. Dimensions in the conveying direction 3' can likewise be assigned to the darkening duration of individual light barriers 5.1 to 5.10, for example, in order to determine a diameter of the container 2.

It is hereby particularly advantageous to measure the time points of the interruption and release of the light barriers 5.1 to 5.10 in at least two height areas H1 to H3 for each container 2 separately and to compare them to one another and/or calculate them together. For example, in the neck area of the containers 2, two such measurements could be carried out in parallel. If a temporal displacement of the interruption and release of the light barriers that are to be compared is registered, this makes it possible to conclude that there is a slanted upright neck area or a container body that is slanted upright with respect to the bottom area of the container 2. For example, this can occur in plastic containers depending on the manufacturing tolerance and in the case of conventional triggering light grids, it can hinder the correct localization of the container main axis 2'. In contrast, according to the present disclosure, a position and/or orientation of the container main axis 2' or other suitable reference points or reference surfaces, for example, in the area of the container bottom, can be determined on the container 2 even in the event of slanted upright containers or container sections. In other words, an intended centric triggering, meaning with respect to an axis of symmetry of the containers 2, can be corrected in this way.

In the event of a change in the sort, meaning a change in the container size, container shape or the container transparency, the light barriers 5.1 to 5.10 can be activated and read out selectively by means of reprogramming the triggering light grid 1. For example, in the event of a change from the smaller container type 2.1 to the larger container type 2.2, additional light barriers 5.7 to 5.10 in the upper area of the triggering light grid 1 can be activated by means of selectively activating the associated light sources 7.7 to 7.10 and reading out the output signals A7 to A10 of the associated light receivers 17.7 to 17.10. Calculation rules for the evaluation of the output signals and/or logical combinations involving individual output signals or output signals evaluated in groups can be adapted here in any way. A mechanical adjustment of the triggering light grid 1, 21, 31 when there is a change in the container sort is consequently made superfluous.

In the case of an unsorted product flow, individual measurement areas of the triggering light grid 1, 21, 31 according to the present disclosure can be selectively or jointly evaluated, in order to identify or measure container types 2.1, 2.2 and/or also to actuate suitable trigger signals TS independently of the respective container type 2.1, 2.2.

The features of the described embodiments 1, 21, 31 can be combined with one another in any technically expedient manner.

What is claimed is:

1. Triggering light grid for at least one of registering the position of containers or checking their alignment on a conveyance path with:
    a plurality of light barriers provided at different height levels with respect to the conveyance path, wherein these light barriers can be activated and read out selectively and separately from one another and that are accommodated in a shared housing; and
    a triggering unit for generating control signals on the basis of output signals of the light barriers, the triggering unit being formed to selectively evaluate the output signals of the read out light barriers periodically within measuring cycles, each with a maximum duration of 2 ms.

2. Triggering light grid according to claim 1 wherein the triggering unit is formed for the selective processing of individual output signals.

3. Triggering light grid according to claim 1 wherein the triggering unit is formed to evaluate the output signals of the activated light barriers periodically within the measuring cycles, each with a maximum duration of 1 ms, in order to assign at least one control signal to each individual container.

4. Triggering light grid according to claim 3, wherein the triggering unit is formed to assign at least one control signal to each individual container.

5. Triggering light grid according to claim 1, wherein the triggering unit is formed to at least one of evaluate or logically combine the output signals of selected light barriers in groups, or to generate at least two control signals assigned to an individual container.

6. Triggering light grid according to claim 1 wherein the distance between neighboring light sources is a maximum of 10 mm.

7. Triggering light grid according to claim 1, furthermore with at least one reflector with which the measurement beams emitted by the light sources can be deflected in the direction of the housing.

8. Triggering light grid according to claim 1 wherein the triggering unit is formed to generate a control signal if at least one of the output signals corresponds to a light attenuation level of at least 5% in the assigned light barrier.

9. Triggering light grid according to claim 1 wherein the light sources are provided such that they are offset in the transport direction of the containers.

10. Triggering light grid according to claim 1 wherein the distance between neighboring light sources is a maximum of 5 mm.

11. Triggering light grid according to claim 1 wherein the triggering unit is formed to generate a control signal if at least one of the output signals corresponds to a light attenuation level of at least 25% in the assigned light barrier.

12. Method for at least one of registering the position of containers or for checking their alignment on a conveyance path, having the triggering light grid according to claim 1, including:
    a) conveying the containers through the triggering light grid;
    b) selectively activating and reading out of individual light barriers and selectively evaluating the output signals of the read out light barriers in order to determine the light attenuation level in at least a stipulated height area of the conveyance path;
    c) comparing the determined light attenuation level with at least one comparison value; and
    d) generating control signals that are assigned to individual containers on the basis of the comparison, output signals of the activated light barriers being evaluated periodically within measuring cycles, each with a maximum duration of 2 ms.

13. Method according to claim 12, wherein the height area is stipulated depending on at least one of the size or shape of a conveyed container type.

14. Method according to claim 13, wherein the output signals are evaluated in groups assigned to height areas in order to determine at least two of the following parameters of the container by means of the light attenuation level in different height areas: height; position in the product flow; characteristic contour; outer diameter; and upright/reclining conveyance orientation.

15. Method according to claim 13 wherein the control signal furthermore is generated on the basis of a measured displacement increment that is characteristic for the conveyance path.

16. Triggering light according to claim 2, wherein the triggering unit is formed in order to process output signals from only those light barriers whose light sources are activated.

17. Method according to claim 12 wherein values of the light attenuation level in at least two height areas are compared or logically processed with one another in order to at least one of identify a container type or distinguish a correct conveyance orientation of the containers from an incorrect conveyance orientation.

18. Method according to claim 12 wherein time points of the interruption and release of the light barriers are measured in at least two height areas and calculated together in order to determine at least one of the position of a reference point, a reference surface, or a main axis of the containers.

19. Method of claim 12, wherein in conveying the containers, the containers are conveyed in an upright orientation.

20. Method according to claim 15, wherein the control signal is indicative of at least one of a container position or a container diameter.

* * * * *